United States Patent
Norcia

[11] Patent Number: 6,033,684
[45] Date of Patent: Mar. 7, 2000

[54] COMPOSITIONS AND METHODS FOR WOUND MANAGEMENT

[75] Inventor: Michael A. Norcia, Safety Harbor, Fla.

[73] Assignee: Jonor, Inc., Clearwater, Fla.

[21] Appl. No.: 09/158,861

[22] Filed: Sep. 23, 1998

Related U.S. Application Data

[63] Continuation-in-part of application No. 08/704,189, Aug. 28, 1996.

[51] Int. Cl.[7] .............................. A61L 15/20; A61L 15/42; A61K 9/10; A61K 9/14; A61K 47/26
[52] U.S. Cl. ......................... 424/448; 424/443; 424/445; 424/484; 514/944
[58] Field of Search ........................... 424/400, 443–448, 424/484–488; 514/944

[56] References Cited

U.S. PATENT DOCUMENTS

| | | |
|---|---|---|
| 2,137,169 | 11/1938 | Levey . |
| 3,339,546 | 9/1967 | Chen . |
| 4,306,551 | 12/1981 | Hymes et al. . |
| 4,307,717 | 12/1981 | Hymes et al. . |
| 4,556,056 | 12/1985 | Fischer et al. . |
| 4,664,105 | 5/1987 | Dautnenberg et al. . |
| 4,675,009 | 6/1987 | Hymes et al. . |
| 4,788,237 | 11/1988 | Le-Khac . |
| 4,875,473 | 10/1989 | Alverez . |
| 4,883,478 | 11/1989 | Lerailler et al. . |
| 4,889,530 | 12/1989 | Smith . |
| 4,891,319 | 1/1990 | Roser . |
| 4,909,243 | 3/1990 | Frank et al. . |
| 4,909,244 | 3/1990 | Quartfont et al. . |
| 4,929,577 | 5/1990 | Cornell . |
| 5,389,383 | 2/1995 | Huth . |

OTHER PUBLICATIONS

Stable Biologicals/BioPharm Jan.–Feb. (1992)—"Letters to the editor".
Stable Biologicals/BioPharm May 36–40 (1992) "Another view of Trehalose for Drying and Stabilizing Biological Materials".
Stable Biologicals/BioPharm Sep. 47–53 (1991)—"Trehalose Drying: A Novel Replacement for Freeze–Drying".

*Primary Examiner*—Edward J. Webman
*Attorney, Agent, or Firm*—Dennis G. LaPointe; Joseph C. Mason, Jr.; Mason & Assoc., P.A.

[57] ABSTRACT

A wound dressing composition and a method of using that composition to enhance the natural process of topical wound healing. The composition comprises at least one adhesive ingredient that adheres to wet skin selected from the hydrocolloid family such as a pectin, an adhesive that adheres to dry skin selected from the families of synthetic and natural elastomers such as polyisobutylene, a hydrophilic compound such as carboxymethylcellulose and a water substitute compound to protect a wound site during dehydration or desiccation, wherein the water substitute compound is trehalose.

12 Claims, No Drawings

COMPOSITIONS AND METHODS FOR WOUND MANAGEMENT

RELATED APPLICATION

This application is a continuation in part of U.S. patent application Ser. No. 08/704,189 filed Aug. 28, 1996.

BACKGROUND OF THE INVENTION

1. Field of the Invention.

This invention relates, generally, to improved methods for wound management using an external wound dressing composition or admixture containing trehalose in combination with adhesives that adhere to wet and dry skin and hydrophilic absorbents. Such compositions uniquely protect living cells and proteins in the wound fluid from desiccation when available water is reduced or removed.

2. Description of Related Art.

As the understanding of the healing process has progressed, various theories have been advanced regarding the most advantageous ways to protect wounds and to optimize the healing process. For many years, absorptive wound dressings, such as a gauze, were used because it was generally believed that wounds required air drying or desiccation to promote epithelial resurfacing without infection. Subsequently, however, it was found that moist conditions were preferable to a dry wound condition for the promotion of healing. Recently, studies have shown that it is preferable to maintain a fluid environment over the wound site in order to promote optimum wound healing. No increase in infection has been associated with wet wound healing.

To provide a device that enhances wound healing is challenging in that wounds are not uniform. Wounds actually have three different areas to consider where wound management is concerned. The first area is the surrounding intact skin. This area is used to fix and adhere the device over the open wound bed. This is where the combination of adhesives that adhere to dry and wet skin must provide adequate skin adhesion, yet be non-adhering to the wound bed. Dressings are commercially available that do this very well and, as such, meet the specific requirement. The second area of concern is the wet wound bed. This area initially will be extremely wet during the inflammatory stage of wound healing and challenge the dressing device to absorb copious amounts of fluid. Again, commercially available dressings contain absorbents, and super absorbents that meet this need. But the problem is that they can absorb too much fluid and dry out the wound bed. This then brings us to the third area of concern, which is the regenerating tissue layer. It is critical that for optimal wound healing to occur, this area must be moist enough for new cells to be adequately supplied with nutrients. If this area becomes dry, then these fragile regenerating cells will die, and the wound healing process will cease. The inclusion of trehalose in wound healing devices is unique in that trehalose will substitutionally bind to cellular proteins, replacing water molecules, thereby protecting them from dehydration during the dehydration process. Trehalose is also selectively effective in the three environments detailed above since its large molecular structure, relative to water, precludes absorption and remains in the wound available as a water substitute.

Other factors must be considered in the development of wound dressings which provide a fluid environment over the wound site. For example, wound dressings must be easily stored and sterilized. Further, wound dressings should be at least toxicologically unobjectionable and be as biocompatible as possible with the human body. Other considerations in the development of wound dressings include sufficient gas permeability for ventilation of vapors from the wound and surrounding skin area; non-adherence to the regenerating tissue of the wound, a high degree of absorbability for wound exudate, bacteria, and necrotic cell material; and as previously stated, the dressing must be conducive to promoting granulation tissue or re-epithelization necessary to provide new skin growth.

It is important to strike a balance between all of these competing factors in the development of wound dressings which promote wound healing. Of particular importance is the balance between a dressing's ability to absorb wound exudate and simultaneously maintain the moisture needed at the wound regrowth site to promote wound healing. Improper moisture maintenance at the wound site can deleteriously effect the healing process. For example, many wound dressings, if allowed to dry over a wound site may stick to the wound. When the stuck dressing is removed from the wound, damage to the integrity of the reepithelized tissue at the wound site may result. Further, if a wound is allowed to dry out due to inadequate coverage by a dressing, the healing process is compromised and reepithelized tissue may dry out and die. It then becomes necessary to remove the dead tissue and again attempt to regain a moist healing environment at the wound site. It has proven particularly difficult to maintain a moist environment at the wound site when the nature of the wound necessitates a wound management protocol that requires frequent dressing changes. This is especially true during the first stages of healing process where there is a high degree of wound exudate and the new dressings have a high initial uptake of liquid.

In an attempt to facilitate wound healing, different dressings and wound management regimes have been developed. Wound management regimes have utilized many materials including gauze, tapes, film dressings, hydrocolloids, gels, foams and saline solutions or other pharmaceutically acceptable carriers in an attempt to promote wound healing. Numerous approaches, having varying degrees of success, have attempted to overcome the deficiencies in the prior art wound dressings which would promote healing. Specifically, various saccharide containing wound dressings have been developed which exhibit excellent moisture absorption capabilities. In addition, saccharides have other beneficial characteristics, such as film forming capabilities, bactericidal effectiveness and they may act as sources of energy. For example, U.S. Pat. No. 4,929,577 to Cornell, U.S. Pat. No. 4,883,478 to Lerailler et al., U.S. Pat. No. 4,788,237 to Le-Khac, U.S. Pat. No. 4,664,105 to Dautzenberg et al., U.S. Pat. No. 4,556,056 to Fischer et al., U.S. Pat. Nos. 4,307,717 and 4,306,551 to Hymes et al. and U.S. Pat. No. 2,137,169 to Levey disclose various saccharide containing wound dressings.

However, in all of these dressings it has proven difficult to strike a balance between their excellent and copious moisture absorption capabilities and the need to maintain enough moisture at the wound regrowth site for the promotion of the healing process, particularly when a fresh dressing is applied. Problematically, these dressings can absorb too much moisture initially, which subsequently causes dehydration of the wound site and loss of structural integrity of cells and protein constituents of the healing wound bed.

In view of the prior art at the time the present invention was made, it was not obvious to those of ordinary skill in the pertinent art how a dressing could simultaneously absorb wound fluid and not damage cells and delicate proteins by excessively removing wound fluid from the wound site.

SUMMARY OF THE INVENTION

In accordance with the present invention, trehalose has a molecular bonding structure similar to water. This protects living cells, protein constituents and biological structures from denaturation during the loss of moisture such as that which may occur upon the application of a new, dry dressing.

In the wound fluid solution, proteins are surrounded by a large amount of hydrogen bonded water molecules that help maintain the precise conformation of the functional protein. When water is removed, proteins become denatured, forming new bonds that lead to aggregation ranging from soluble but inactive microaggregates to gross insoluble precipates in the wound. If the hydration shell is removed, the conformity, specificity, and affinity of the antibodies, growth factors, enzymes, cells and other proteinaceous constituents is altered and loss of function results. This causes the healing cascade to pause and reproduce replacements for the inactivated cells and proteins.

The protective function of trehalose is to substitute for water as the water content of the wound bed cycles up and down due to factors such as absorptive dressing changes. Trehalose is a disaccharide chemically known as α-D-glucopyranosyl-α-D-glucopyranoside. The unique physical properties of trehalose such as high solubility, lack of chemical reactivity and absence of toxicity presents a collection of properties that provide a surprising extension to the functionality of cell growth factors, lipoproteins and other proteinaceous building blocks needed for wound repair.

The present invention discloses the inclusion of trehalose in wound dressings commercially available, and future wound dressings as well. Trehalose, as presented herein, is to be incorporated in an amount sufficient to protect living skin cells, proteins, protein constituents and biological structures at the wound regrowth site from dehydration, desiccation, and tissue death by substituting trehalose molecules for water molecules when available water is reduced or absent.

The invention accordingly will be exemplified in the description hereinafter set forth, and the scope of the invention will be indicated in the claims.

DETAILED DESCRIPTION OF THE INVENTION

Trehalose useful in the present invention has the following chemical formula:

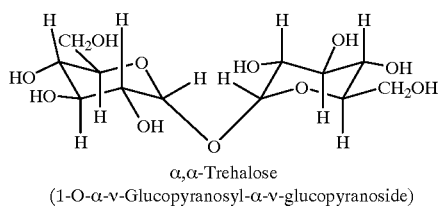

α,α-Trehalose
(1-O-α-v-Glucopyranosyl-α-v-glucopyranoside)

The following examples and descriptions will now more fully illustrate and explain certain and various embodiments of the present invention, all parts and percentages therein being by weight, unless otherwise noted. The wound dressings associated with this novel present invention are made according to processes generally known in the art.

EXAMPLE 1

A typical hydrocolloid absorptive adhesive wound dressing formulation is outlined below.

| Component | Percent | Function |
| --- | --- | --- |
| Polyisobutylene | 55 | dry skin adhesive |
| Pectin | 20 | wet skin adhesive |
| Carboxymethycellulose | 10 | absorbent |
| Guar gum | 10 | thickener and binding agent |
| Polybutene | 2 | tackifier |
| Trehalose | 3 | water substitute cell protectant |

The amount of trehalose which may be used in the above formulation may vary from 0.1% to 5.0%.

When the formulation is placed over a wound site, the dry and wet adhesive will adhere to the intact skin surrounding the wound so as to hold the dressing in place over the wound bed. The absorbents will absorb excess wound fluid in an attempt to maintain optimum moisture content in the wound bed. If the absorbents absorb too much fluid, the wound bed will become dehydrated.

In the wound dressing formulations without trehalose, living cells will die. But because trehalose is topically added to this typical formulation, living cells are protected by the molecular substitution of trehalose for water. When water is replenished to the wound site, water molecules, will replace trehalose and cell growth will reoccur.

An oxygen and vapor-permeable outer thin film layer with an adhesive coating may be laminated to the trehalose hydrocolloid formulation on at least a portion thereof for added comfort to the user and if extended beyond the borders of the hydrocolloid, may enhance adhesion to dry skin. The outer sheet, which may be made out of any suitable materials, such as ethylene vinyl acetate, and is from 1 to 10 mils thick, serves as a support for the dressing prior to application. In addition, it serves as a moisture barrier to prevent drying of the hydrocolloid for dressing during the dressing's shelf life. However, where the components of the dressing possess sufficient dimensional stability, the outer layer may be eliminated, and a protective moisture barrier during storage may be provided by suitable packaging such as, metal foil, plastic wrap or other suitable packaging known to those skilled in the art.

The dressing may contain other components, compounds or ingredients for performing specific desired additional functions; for example, super absorbents, tackifiers, fillers, bactericides, medicants, or other bioactive agents.

The outer oxygen- and vapor-permeable layer, also serves as a bacterial barrier, and is preferably transparent. Suitable films, adhesives and their preparations are described, for example, in U.S. Pat. No. 3,645,835, which is incorporated herein by reference. Adhesive coated oxygen- and vapor-permeable layer should preferably have a water vapor transmission rate (WVTR) of at least 250 g/m²/24 hrs (40° C., 80% relative humidity (RH)). Especially preferred are such adhesive coated oxygen- and vapor-permeable films with a WVTR of about 400 to 500 g/m²/24 hrs in which the backing material is a transparent polyurethane film having a thickness of about 0.5 to 2 mils (13 to 51 microns) and the film is coated with a 1 mil (25 microns) layer of pressure-sensitive acrylic ester copolymer adhesive.

The outer-film layer is typically made from synthetic polymers and non-woven and woven materials which are capable of being formed into continuous films by casting, extrusion or other known film making processes. The film is also preferably conformable to body surfaces. Conformability is somewhat dependent on thickness, thus the thinner the film the more conformable it is. In a preferred embodiment the film thickness is from 0.5 to 5 mils. Films of this type are known in the art and generally are hydrophilic, polymeric materials such as polyether block amides, copolymers of cyclic polyesters, elastomeric polyesters, blends of polyurethane and polyester, chlorinated polyethylene, styrene/butadiene block copolymers, polyvinyl chloride and other commercial polyurethane compositions. Nonwoven sheet materials with pore diameters below twenty (20) microns are useful in the present invention. Alternatively, films coated on one face with a thin bacteria proof layer of polymer can also be used. Further, the film may be continuous in that it has no perforations or pores in the body contacting portion of the film.

The adhesive coating may be selected from any number of commercially available medical grade adhesives known in the art. For example, multipolymer emulsions comprising stable pressure-sensitive aqueous acrylic adhesives having a solids content of 59% and a viscosity of 1,500-Z, 300 CPS are useful in the present invention. The adhesive properties of medical grade adhesives can be adjusted by the addition of a greater amount of cross-linking additives and/or by utilizing different coating weights and/or viscosities of the adhesive materials.

The adhesive coating may contain other components or reagents for performing specific desired functions, for example, tackifiers, fillers, bactericides, medicaments or other bioactive agents. The adhesive coating should be as thin as possible while functioning to adhere the dressing to the skin. Preferably it is from 1 to 15 mils thick.

Generally, a release sheet, preferably silicone release paper, is releasably secured to protect the skin contact hydrocolloid dressing element prior to application of the dressing to a wound site. During application, the release sheet is removed, the dressing is then applied to the wound, and finally, the removable outer sheet is removed. Specifically, the release sheet can be made from numerous commercially available silicone or teflon coated release sheets known in the art. Base polymers and papers, such as polyester, polypropylene, polyethylene, styrene, unbleached and bleached kraft papers which can be clay coated or uncoated are also useful in the present invention. Numerous materials known in the art would be suitable based on factors including the need for transparency, stiffness and release force from a chosen adhesive. Additionally, the release sheet can be made of polyethylene, polypropylene or polyester which is coated with a releasing agent such as silicone or fluorochemicals. Preferred release layers are silicone coated.

The absorbent dressing component or compound may be made of natural and synthetic polymeric absorbents, hydrocolloid/polysaccharide absorbents, cellulosic absorbents, gum absorbents, resin absorbents, inorganic absorbents and hydrogel absorbents. Hydrogels which are particularly useful in the present invention in general possess the ability to absorb and retain large quantities of liquid such as wound exudate. For example, U.S. Pat. No. 4,300,820 to Shah, which is incorporated herein by reference, relates to a class of absorbing hydrogels useful for wound dressings which can absorb more that 45 percent of their weight of water. Other useful absorbing hydrogels include those disclosed in U.S. Pat. Nos. 3,419,006, 3,664,343 and 3,993,551, which are incorporated herein by reference. Other absorbing hydrogels useful for this dressing formulation include a polymer of 2-acrylamido-2-methylpropane sulfonic acid or a salt thereof disclosed in U.S. Pat. Nos. 4,391,278 and 4,242,242 which are incorporated herein by reference. The dressing is from 5 to 250 mils thick, and preferably from 50 to 150 mils thick.

EXAMPLE 2

A typical hydrogel wound dressing formulation is outlined below:

| Component | Percent | Function |
| --- | --- | --- |
| Distilled water | 87 | solvent |
| Glycerin | 5 | humectant |
| Starch Copolymer | 3 | gelling agent |
| Trehalose | 5 | water substitute cell protectant |

The amount of trehalose which may be used in the above formulation may vary from 0.05% to 20%.

The hydrogel formulation would generally be applied directly into the wound usually after the initial stages of wound healing when wounds have a tendency to dry out. The intention of the hydrogel is to keep the wound bed moist. In typical hydrogel formulations without trehalose, the hydrogel may not adequate provide sufficient moisture to maintain living cells or support the regeneration of new cell growth. If this occurs, cells will dehydrate, denature and die. But because trehalose is added to this typical formulation, living cells are protected by the molecular substitution of trehalose for water. When water is replenished to the wound site, water molecules will replace trehalose and cell growth can reoccur.

EXAMPLE 3

A typical dry powder wound dressing formulation is outlined below.

| Component | Percent | Function |
| --- | --- | --- |
| Karaya Gum | 50 | absorbent and gel former |
| Pectin | 30 | wet skin adhesive |
| Trehalose | 20 | water substitute cell protectant |

The amount of trehalose, which may be used in the above formulation, may range from 5% to 50%. The dry trehalose component should be of a powder of a particle size from 60 mesh to 200 mess (Tyler), preferably about 150 mesh.

The typical powder combination is applied directly to the wet wound site. The karaya acts as the main wound fluid absorbent while in combination with the pectin, forms an adhesive gel to maintain a moist wound environment in the wound bed. In typical powder formulations, the absorbents may absorb an excess amount of wound fluid, causing the wound to dry out resulting in cellular death. However, with the addition of trehalose, living cells are protected by the molecular substitution of trehalose for water. When water is replenished to the wound site, water molecules will replace trehalose and cell growth can reoccur.

The wound dressings of the present invention are particularly useful in wound management regimes that require frequent dressing changes. The dressings of the present invention facilitate the overall outward movement of wound exudate while maintaining the moisture content of the wound epithelium and surrounding skin as do typical commercially available absorptive dressings, but the inclusion of trehalose in such formulae protects living cells from the effects of over absorbing wound fluids.

It will thus be seen from the foregoing description, that certain changes may be made without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A self adhesive topically applied wound site dressing comprising an admixture of:

an adhesive that adheres to dry skin;

an adhesive that adheres to wet skin;

a moisture absorbing hydrophilic compound; and trehalose in an amount sufficient to protect the wound site during dehydration or desiccation and from the effects of dehydration or desiccation.

2. The self adhesive topically applied wound site dressing admixture according to claim 1, wherein the trehalose is in a normal saline carrier.

3. A self adhesive topically applied wound dressing for enhancing the healing of a wound site comprising an admixture of:

at least one adhesive that adheres to dry skin;

at least one adhesive that adheres to wet skin;

at least one moisture absorbing hydrophilic compound; and a water substitute compound comprising trehalose in an amount sufficient to protect the wound site from dehydration or desiccation and from the effects of dehydration or desiccation.

4. The self adhesive topically applied wound dressing admixture for enhancing the healing of a wound site according to claim 3, further including a normal saline carrier.

5. A method for enhancing the healing of a wound site which comprises:

topically applying to the site of the wound, a wound healing factor protectant comprising an admixture of:
   (a) at least one adhesive that adheres to dry skin;
   (b) at least one adhesive that adheres to wet skin;
   (c) at least one moisture absorbing hydrophilic compound; and
   (d) a water substitute compound comprising trehalose in an amount sufficient to protect the wound site during dehydration or desiccation and from the effects of dehydration or desiccation.

6. The method for enhancing the healing of a wound site according to claim 5, further including a normal saline carrier.

7. A method for protecting a wound site during dehydration or desiccation of said wound site which comprises topically applying trehalose in a pharmaceutically acceptable carrier.

8. The method for enhancing the healing of a wound site according to claim 5, wherein the wound healing factor protectant constitutes a wound dressing.

9. A method for enhancing the healing of a wound site comprising the topical administration of a self adhesive wound site dressing to said wound site, comprising an admixture of:

an adhesive that adheres to dry skin;

an adhesive that adheres to wet skin;

a moisture absorbing hydrophilic compound; and trehalose in an amount sufficient to protect the wound site from dehydration or desiccation and from the effects of dehydration or desiccation.

10. A method for protecting a wound site during dehydration or desiccation of said wound site which comprises topically applying to the site of the wound, a wound dressing comprising an admixture of:

an adhesive that adheres to dry skin;

an adhesive that adheres to wet skin;

a moisture absorbing hydrophilic compound;

a trehalose; and a pharmaceutically acceptable carrier.

11. The method for protecting a wound site during dehydration or desiccation of said wound site according to claim 10, wherein the trehalose is present in an amount sufficient to protect the wound site from dehydration or desiccation.

12. A method of enhancing the healing of a wound site comprising the topical administration of a gel to the wound site, comprising an admixture of:
    (a) at least one adhesive that adheres to wet skin;
    (b) at least one gel forming agent;
    (c) at least one moisture absorbing hydrophilic compound; and
    (d) a water substitute compound comprising trehalose in an amount sufficient to protect the wound site from dehydration or desiccation.

* * * * *